United States Patent [19]

Moeller et al.

[11] Patent Number: 4,942,174
[45] Date of Patent: Jul. 17, 1990

[54] NOVEL SEBOSUPPRESSIVE COMPOUNDS AND PREPARATIONS

[75] Inventors: Hinrich Moeller; Siegfried Wallat, both of Monheim, Fed. Rep. of Germany

[73] Assignee: Henkel Kommanditgesellschaft auf Aktien, Duesseldorf-Holthausen, Fed. Rep. of Germany

[21] Appl. No.: 269,940

[22] Filed: Nov. 10, 1988

[30] Foreign Application Priority Data

Nov. 12, 1987 [DE] Fed. Rep. of Germany ....... 3738407

[51] Int. Cl.$^5$ ............................................. C07C 69/76
[52] U.S. Cl. .................................. 514/532; 514/570; 514/880; 514/881; 560/55; 562/465
[58] Field of Search ................... 560/55; 562/465; 514/532, 570

[56] References Cited

FOREIGN PATENT DOCUMENTS 3121091 8/1983 Fed. Rep. of Germany .

OTHER PUBLICATIONS

CA 88(17): 120815h Japan Kokai JP 52/133944, Nov. 9, 1977.

Primary Examiner—Paul J. Killos
Attorney, Agent, or Firm—Ernest G. Szoke; Wayne C. Jaeschke; Norvell E. Wisdom, Jr.

[57] ABSTRACT

Novel alkyl aryl ether derivatives corresponding to the formula:

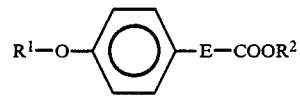

in which $R^1$ is a $C_8$–$C_{20}$ alkyl group with one or more branches, E is a group —$CH_2$—$CH_2$— or —CH=CH— and $R^2$ is a $C_1$–$C_4$ alkyl group, a $C_2$–$C_4$ hydroxyalkyl group, an alkoxyalkyl group containing 1 to 4 C atoms in the alkoxy group and 2 to 4 C atoms in the alkyl group, hydrogen or a salt-forming cation, are highly effective sebosuppressive agents in cosmetic or pharmaceutical preparations for topical application to the hair and to the skin.

20 Claims, No Drawings

NOVEL SEBOSUPPRESSIVE COMPOUNDS AND PREPARATIONS

FIELD OF THE INVENTION

This invention relates to new p-alkoxyarylcarboxylic acids, salts and esters thereof that are antiseborrhoeic agents and to their use for the production of topical, pharmaceutical or cosmetic sebosuppressive preparations.

DESCRIPTION OF RELATED ART

Excessive secretions of the sebaceous glands of the epidermis can lead to skin disorders. In mild cases, which occur fairly frequently, these excessive secretions cause a greasy appearance of the hair or a shiny, oily appearance of the skin. Accordingly, efforts are being made in modern cosmetics and toiletries, hereinafter jointly called cosmetics for convenience and brevity, to avoid excessive secretions of the sebaceous glands by suitable topical preparations and thus to promote an attractive appearance of the hair and skin after using the cosmetics. Furthermore, in severe cases seborrhoea can become a medical problem, for which appropriate therapy is needed.

Antiseborrhoeic additives which have already been taught for cosmetic preparations include 4-alkoxybenzoic acid esters (German patent application Nos. DE-A 31 21 064, DE-A 35 00 971 and European patent application No. EP-A 114 051), 4-alkoxy-benzoic acids and salts thereof (German patent application Nos. DE-A 30 47 106 and DE-A 35 00 972), linear alkoxycinnamic acid esters (German patent application No. DE-A 31 21 091) and $C_1$-$C_6$ alkoxyphenylpropionic acid esters (German patent application No. DE-A 30 47 106).

Although the compounds disclosed in the cited publications show a distinct antiseborrhoeic effect, there is still a need for preparations which show increased activity for low in-use concentrations.

DESCRIPTION OF THE INVENTION

Except in the operating examples, all numbers herein expressing quantities of materials or reaction conditions are to be understood as if modified by the word "about".

Novel compounds that show good antiseborrhoeic activity at concentrations of only 0.01% by weight and lower in vehicles suitable for topical application have been discovered. These compounds are alkoxyarylcarboxylic acids, salts and esters thereof corresponding to the following general formula:

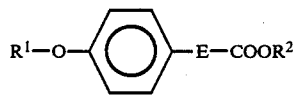

$$R^1-O-\text{\textlangle}\bigcirc\text{\textrangle}-E-COOR^2 \quad (I)$$

in which $R^1$ is a $C_8$-$C_{20}$ alkyl group with one or more branches, E is a group $-CH_2-CH_2-$ or $-CH=CH-$, and $R^2$ is a $C_1$-$C_4$ alkyl group, a $C_2$-$C_4$ hydroxyalkyl group, an alkoxyalkyl group containing 1 to 4 C atoms in the alkoxy group and 2 to 4 C atoms in the alkyl group, hydrogen or a salt-forming cation.

In the compounds corresponding to formula (I), $R^1$ may be, for example, a 2-ethyl hexyl, 3,3,5-trimethyl pentyl (=isooctyl), 3,5,5-trimethyl hexyl (=isononyl), isodecyl, isotridecyl, 2-butyl octyl, 2-hexyl decyl, isoheptadecyl, isostearyl or 2-octyl dodecyl group. The single-branch alkyl groups are usually derived from alcohols obtained by aldol condensation from aldehydes and hydrogenation of the aldol adduct or from alcohols obtained by Guerbert dimerization from linear, primary alcohols. Alkyl groups having more than one branch are derived from alcohols obtained by oxosynthesis (hydroformylation) from branched olefins which in turn may be obtained by oligomerization of lower olefins, for example diisobutylene, tripropylene, tetrapropylene, triisobutylene, pentapropylene, etc.

$R^2$ is preferably hydrogen or a salt-forming cation. Particularly suitable are dermatologically compatible salts, such as the alkali and alkaline earth salts, for example the sodium, potassium, calcium or magnesium salts, and also the ammonium and alkanolammonium salts, for example the monoethanolammonium, the isopropanolammonium or the triethanolammonium salt. However, salts of other bases are also effective providing they show adequate dermatological compatibility.

Although the p-alkoxyarylcarboxylic acids, their salts and esters of formula (I) are new, as compounds of the basic type known from the cited prior art they may be obtained by the general synthesis processes known from the literature described in that prior art.

The p-alkoxyarylcarboxylic acid methyl esters are prepared, for example, by alkylation of p-hydroxycinnamic acid methyl ester or p-hydroxyphenylpropionic acid methyl ester with halides of the formula $R^1$-X (where X is chlorine or bromine for example) or with corresponding sulfates or sulfonic acid esters which may be obtained from the corresponding alcohols by methods known from the literature.

The hydroxyalkyl and alkoxyalkyl esters may be prepared from the corresponding p-alkoxyarylcarboxylic acid methyl esters by transesterification with the particular alcohol components $R^2$OH in the presence of alkaline catalysts, such as for example sodium alcoholates.

Conversely, the esterification of the p-hydroxyarylcarboxylic acids may be carried out first, followed by alkylation.

The free acids, in which $R^2$ is hydrogen, may readily be obtained from the corresponding methyl esters by saponification (hydrolysis). They may be converted by neutralization with bases into the salts in which $R^2$ is the salt-forming cation.

The p-alkoxyarylcarboxylic acids, their salts and esters corresponding to formula (I) show pronounced sebosuppressive activity, many of the products developing a significant sebostatic and antiseborrhoeic effect on the skin even in very low in-use concentrations. In addition, they show excellent compatibility with the skin and mucous membrane. The alkoxyarylcarboxylic acids and their derivatives of formula (I) are preferably used in a quantity of 0.0005 to 2.0% by weight in suitable vehicles. They may readily be incorporated in various pharmaceutical and cosmetic vehicles.

Suitable cosmetic vehicles are any preparations suitable for application to the hair or to the skin. Aqueous or alcoholic solutions, emulsions, creams, gels and stick preparations are particularly suitable for the treatment of skin. Hair lotions, hair shampoos, hair tonics, hair rinses and hair sprays are particularly suitable for the treatment of hair. On account of the particular cosmetic problems caused by greasy hair, the hair-treatment preparations represent a particularly preferred embodiment of the invention.

The most important components of typical cosmetic vehicles are:

(1) oil components, for example paraffin oil, vegetable oils, fatty acid esters, squalene, fatty alcohols, or 2-octyl dodecanol;

(2) fats and waxes, for example spermaceti, beeswax, montan wax, paraffin, or cetostearyl alcohol;

(3) emulsifiers, for example fatty acid partial glycerides, fatty acid sorbitan partial esters and ethoxylates thereof, soaps, fatty alcohol sulfates, fatty alcohol polyglycol ethers, or alkylphosphates;

(4) detergents effective for soil removal during washing, particularly (4.1) anionic surfactants, such as fatty alcohol polyglycol ether sulfates, fatty alcohol sulfates, alpha-olefin sulfonates, alkanesulfonates, sulfosuccinic acid esters, acyl taurides, acyl isothionates, and acyl sarcosines; (4.2) ampholytic surfactants, such as N-alkyl glycine, N-alkylaminopropionic acid, N-alkylaminobutyric acid containing 8 to 18 C atoms in the alkyl group; (4.3) zwitterionic surfactants, such as example N-alkyl-($C_8$–$C_{18}$)-N,N-dimethylammonioglycinate or N-"coconut-acyl"-aminopropyl-N,N-dimethylammonioglycinate, where "coconut-acyl" refers to acyl groups derived from the naturally occurring mixture of long chain carboxy fragments in coconut oil; (4.4) nonionic surfactants, such as fatty alcohol polyglycol ethers, alkylphenol polyglycol ethers, fatty acid polyglycol esters, amine oxide surfactants, fatty acid alkanolamides and ethoxylates thereof; and (4.5) cationic surfactants, such as alkyl ($C_{12}$–$C_{18}$) trimethylammonium chloride, lauryl dimethyl benzylammonium chloride, cetylpyridinium chloride, distearyl dimethylammonium chloride;

(5) lower alcohols, such as ethanol or isopropanol;

(6) polyhydric alcohols, such propylene glycol, or glycerol;

(7) water and auxiliaries, such as perfumes, preservatives, buffers, thickeners, dyes and opacifiers.

Testing and evaluation of the antiseborrhoeic effect

Basis

The test is based on the observation that male rats secrete a brownish sebum so that the degree of greasiness of the skin may readily be visually assessed as browning of the skin. The fact that the browning involves sebum is reflected in the fact that young female rats and male rats washed with surfactant solutions or with lipid solvents, or even male rats systematically treated with estrogen, only show the normal light, pink-colored skin after shearing. At the same time, only very small quantities of lipids can be extracted from the hair cut off; cf. J. Soc. Cosmet. Chem. 34, 127–135 (1983)).

Procedure

Male Wistar rats having a body mass of 220 to 230 grams at the beginning of the test were used as the test animals. The test substances, dissolved in a mixtures of equal volumes of ethanol and acetone, were brushed onto half of the back of each of 6 rats for each substance and concentration tested. The other half of the back of each tested rat was treated with the solvent only. One application was made on each tested rat on each of Monday through Friday of one week and on each of Monday through Thursday in the next week; the rats were then evaluated on Friday of the second week. For evaluation, the rats were shaved on their backs and flanks and visually assessed independently by a panel of examiners (6 people) under double-blind conditions. The degree of browning on the backs of the rats was visually assessed as a measure of the sebum coating. A group of six rats of the same type treated on both sides with the solvent only was used for control.

Scoring

The intensities of the brown color on each control rat, and on the side of each other tested rat that had been treated with a solution containing a substance to be tested for its sebosuppressive ability, were scored according to the following scale:

3 points: dark brown
2 points: mid-brown
1 point: light brown
0 point: no browning.

The sum of the scores for the six treated rats in each group was divided by the sum of the scores for the six control rats for that group, this quotient was multiplied by 100, and that result subtracted from 100, to give the percentage sebum reduction as recorded in the tables below.

EXAMPLES OF PRACTICE OF THE INVENTION

The following non-limiting examples and comparison examples are intended to illustrate the invention.

1. Examples of Synthesis of Compounds of the Invention 1.1 Isononyloxycinnamic acid methyl ester Methanol was removed by distillation from a mixture of 14.2 g (79.7 mmol) 4-hydroxycinnamic acid methyl ester, 150 ml N-methylpyrrolidone and 14.4 g (79.7 mmol) 30% sodium methylate solution in methanol, then 0.5 g tetrabutylammonium chloride and 15.5 g (95.6 mmol) isononyl chloride were added. The addition was followed by heating with stirring for 8 hours to 160 C. After cooling to room temperature, the solution was filtered off from the sodium chloride formed, concentrated to dryness under reduced pressure, the evaporation residue taken up in methylene chloride, washed with water, dried with sodium sulfate and, after concentration by evaporation, chromatographed on silica gel (Merck) (eluent: methylene chloride/toluene =8.2). 20.1 g (91% of the theoretical) 4isononyloxycinnamic acid methyl ester were obtained in the form of a colorless oil having a refractive index at 20 C of 1.5414.

1.2 4-isotridecyloxycinnamic acid methyl ester (refractive index at 20° C.: 1.5334) was prepared from isotridecyl chloride, substituted on an equimolar basis for isononyl chloride, by the method described in 1.1.

1.3 4-(2-ethylhexyl)-oxycinnamic acid methyl ester (refractive index at 20° C.: 1.5471) was prepared from 2-ethylhexyl chloride, substituted on an equimolar basis for isononyl chloride, by the method described in 1.1.

1.4 3-(4-isononyloxyphenyl)-propionic acid methyl ester (refractive index at 20° C. : 1.4904) was prepared from 3-(4-hydroxyphenyl)-propionic acid methyl ester, substituted on an equimolar basis for 4-hydroxycinnamic acid methyl ester, and isononyl chloride by the method described in 1.1.

1.5 3-(4-isotridecyloxyphenyl)-propionic acid methyl ester (refractive index at 20° C. : 1.4902) was prepared from 3-(4-hydroxyphenyl)-propionic acid methyl ester, substituted on an equimolar basis for 4-hydroxycinnamic acid methyl ester, and isotridecyl chloride, substituted on an equimolar basis for isononyl chloride, by the method described in 1.1.

Samples of the esters prepared in examples 1.1–1.5 were hydrolyzed by the following procedure:

A mixture of 52.6 mmol of the ester, 55 ml ethanol, 40 ml water and 2.5 g sodium hydroxide was heated for 2 hours to the boiling temperature, concentrated by evaporation, ice and water mixture added, and the mixture acidified with 2 M hydrochloric acid. After extraction three times by shaking with methylene chloride, concentration by evaporation and recrystallization of the residue from n-hexane, the acids described below were obtained in an almost quantitative yield. Thus prepared were:

1.6 4-isononyloxycinnamic acid (colorless solid melting at 128° to 132° C.)

1.7 4-(2-ethylhexyl)-oxycinnamic acid (melting point: 80° to 81° C.)

1.8 isotridecyloxycinnamic acid (melting point: 75°–91° C.)

1.9 3-(4-isotridecyloxyphenyl)-propionic acid (liquid with refractive index at 20° C. of 1.4990)

1.10 3-(4-isononyloxyphenyl)-propionic acid (melting point: 63°–65° C.)

The percentage of sebum reduction, measured as described above, for solutions of the compounds made in Example 1.1 to 1.9 are shown in Table 1. The following n compounds were tested for comparison, with results shown in Table II.

C 1.11: 4n-decyloxycinnamic acid methyl ester
C 1.12: 4-n-decyloxyphenylpropionic acid methyl ester
C 1.13: 4-isononyloxybenzoic acid methyl ester
C 1.14: 4-isotridecyloxybenzoic acid methyl ester
C 1.15: 4-isotridecyloxyphenyl acetic acid methyl ester
C 1.16: 4-isononyloxybenzoic acid
C 1.17: 4-isotridecyloxybenzoic acid

TABLE I

| Product of Example No. | Concentration, % by weight | Percentage sebum reduction |
| --- | --- | --- |
| 1.1 | 0.01 | 46 |
| 1.1 | 0.1 | 98 |
| 1.2 | 0.01 | 28 |
| 1.2 | 0.1 | 100 |
| 1.3 | 0.1 | 31 |
| 1.3 | 0.5 | 67 |
| 1.4 | 0.1 | 100 |
| 1.5 | 0.1 | 100 |
| 1.6 | 0.005 | 35 |
| 1.6 | 0.01 | 72 |
| 1.7 | 0.05 | 24 |
| 1.7 | 0.1 | 82 |
| 1.8 | 0.002 | 20 |
| 1.8 | 0.01 | 82 |
| 1.9 | 0.005 | 23 |
| 1.10 | 0.05 | 55 |

TABLE II
(Comparisons)

| Comparison Products | Concentration % by weight | Percentage sebum reduction |
| --- | --- | --- |
| C 1.11 | 0.1 | 11 |
| C 1.12 | 0.05 | 12 |
| C 1.13 | 0.1 | 26 |
| C 1.14 | 0.01 | 0 |
| C 1.15 | 0.1 | 0 |
| C 1.16 | 0.02 | 21 |
| C 1.17 | 0.002 | 0 |

What is claimed is:

1. In a preparation intended for topical application to human skin, the improvement comprising the presence, in a sebosuppressive effective amount, of an alkyl aryl ether corresponding to the formula:

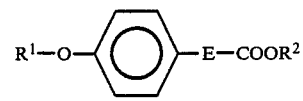

in which $R^1$ is a $C_8$–$C_{20}$ alkyl group with at least one branch, E is either $-CH_2-C_2$ or $-CH=CH-$, and $R^2$ is selected from the group consisting of a $C_1$–$C_4$ alkyl group, a $C_2$–$C_4$ hydroxyalkyl group, an alkoxyalkyl group containing 1 to 4 C atoms in the alkoxy group and 2 to 4 C atoms in the alkyl group, hydrogen, and a salt-forming cation.

2. A process for treating human skin or hair, comprising topically applying to said skin a preparation according to claim 1.

3. A preparation according to claim 1, wherein $R^1$ is a $C_8$–$C_{13}$ alkyl group and $R^2$ is selected from the group of methyl, hydrogen, and a salt forming cation.

4. A preparation according to claim 3, wherein said alkyl aryl ether is Isononyloxycinnamic acid methyl ester.

5. A preparation according to claim 3, wherein said alkyl aryl ether is 4-isotridecyloxycinnamic acid methyl ester.

6. A preparation according to claim 3, wherein said alkyl aryl ether is 4-(2-ethylhexyl)-oxycinnamic acid methyl ester.

7. A preparation according to claim 3, wherein said alkyl aryl ether is 3-(4-isononyloxyphenyl)-propionic acid methyl ester.

8. A preparation according to claim 3, wherein said alkyl aryl ether is 3-(4-isotridecyloxyphenyl)-propionic acid methyl ester.

9. A preparation according to claim 3, wherein said alkyl aryl ether is Isononyloxycinnamic acid.

10. A preparation according to claim 3, wherein said alkyl aryl ether is 4-isotridecyloxycinnamic acid.

11. A preparation according to claim 3, wherein said alkyl aryl ether is 4-(2-ethylhexyl)-oxycinnamic acid.

12. A preparation according to claim 3, wherein said alkyl aryl ether is 3-(4-isononyloxyphenyl)-propionic acid.

13. A preparation according to claim 3, wherein said alkyl aryl ether is 3-(4-isotridecyloxyphenyl)-propionic acid.

14. A process for treating human skin, comprising topically applying to said skin a preparation according to claim 13.

15. A process for treating human skin, comprising topically applying to said skin a preparation according to claim 11.

16. A process for treating human skin, comprising topically applying to said skin a preparation according to claim 9.

17. A process for treating human skin, comprising topically applying to said skin a preparation according to claim 8.

18. A process for treating human skin, comprising topically applying to said skin a preparation according to claim 7.

19. A process for treating human skin, comprising topically applying to said skin a preparation according to claim 5.

20. A process for treating human skin, comprising topically applying to said skin a preparation according to claim 4.

* * * * *